United States Patent
Rethore et al.

(10) Patent No.: US 8,227,514 B2
(45) Date of Patent: Jul. 24, 2012

(54) TOPICAL APPLICATION OF TRAVOPROST FOR COMBATING HAIR LOSS

(75) Inventors: Sandrine Rethore, Valbonne (FR); Carine Rosignoli, Biot (FR); André Jomard, Saint Vallier de Thiey (FR); Johannes Voegel, Chateauneuf/Grasse (FR)

(73) Assignee: Galderma Research & Development, Biot (FR)

( * ) Notice: Subject to any disclaimer, the term of this patent is extended or adjusted under 35 U.S.C. 154(b) by 63 days.

(21) Appl. No.: 12/710,382

(22) Filed: Feb. 23, 2010

(65) Prior Publication Data

US 2010/0190853 A1    Jul. 29, 2010

Related U.S. Application Data

(63) Continuation of application No. PCT/FR2008/051539, filed on Aug. 28, 2008.

(30) Foreign Application Priority Data

Aug. 28, 2007 (FR) .................................. 07 57208

(51) Int. Cl.
*A61K 31/5575* (2006.01)
(52) U.S. Cl. ....................................................... 514/573
(58) Field of Classification Search .................. 514/573
See application file for complete search history.

(56) References Cited

U.S. PATENT DOCUMENTS

| 2007/0059265 A1 | 3/2007 | Boulle |
| 2007/0078175 A1 | 4/2007 | Boulle et al. |
| 2007/0160562 A1 | 7/2007 | Brinkenhoff |

FOREIGN PATENT DOCUMENTS

| EP | 1739083 A1 | 1/2007 |
| EP | 1775294 A1 | 4/2007 |
| WO | WO 03/009820 A2 | 2/2003 |

OTHER PUBLICATIONS

Johnstone et al. (Survey of Ophthalmology, vol. 47, Supp. 1, pp. S185-S202; 2002).*
Hollo (Expert Opin. Drug Saf., vol. 6, No. 1, pp. 45-52; Jan. 2007).*
Barnebey et al., "The Safety and Efficacy of Travoprost 0.004%/Timolol 0/5% Fixed Combination Ophthalmic Solution", American Journal of Ophthalmology, 2005, pp. 1e1-1e8, vol. 140, No. 1, Ophthalmic Publ., Chicago, IL.
Feletti et al., "Periocular pigmentation associated with use of travoprost for the treatment of alopecia areata of the eyelashes", Journal of the European Academy of Dermatology & Venereology, 2007, pp. 421-423, vol. 21, No. 3, Elsevier Science Publ., Amsterdam, NL.
English language International Search Report from corresponding International Application No. PCT/FR2008/051539, mailed on Mar. 5, 2009.

* cited by examiner

*Primary Examiner* — Jeffrey S. Lundgren
*Assistant Examiner* — Nelson C Blakely, III
(74) *Attorney, Agent, or Firm* — SNR Denton US LLP

(57) ABSTRACT

Travoprost medicament compositions for non-daily topical application are useful for simulating or inducing the growth and/or decreasing the loss and/or increasing the density and/or reducing the heterogeneity in the diameter of human hair shafts/follicles, e.g., for the treatment of androgenic alopecia, such medicament compositions being at least twice applied over a time interval of greater than 24 hours.

10 Claims, 3 Drawing Sheets

| Anova Test Results | p Value | Significance |
|---|---|---|
| Travoprost at 1μM in repeat treatment | 0.02 | * |
| Travoprost at 1μM in single treatment | 0.007 | ** |

TOPICAL APPLICATION OF TRAVOPROST FOR COMBATING HAIR LOSS

CROSS-REFERENCE TO EARLIER APPLICATIONS

This application is a continuation of PCT/FR 2008/051539, filed Aug. 28, 2008 and designating the United States (published in the French language on Mar. 12, 2009 as WO 2009/030862 A2; the title and abstract were also published in English), which claims priority under 35 U.S.C. §119 of application Ser. No. 07/57208, filed in France on Aug. 28, 2007, each earlier application hereby expressly incorporated by reference in its entirety and each assigned to the assignee hereof.

BACKGROUND OF THE INVENTION

1. Technical Field of the Invention

The present invention relates to the formulation of travoprost compositions useful to induce or stimulate the growth of hair shafts and in particular, human hair and eyelashes.

2. Description of Background and/or Related and/or Prior Art

In human beings, the growth of the hair is cyclical and comprises three successive phases: the anagen phase, the catagen phase and the telogen phase. Each follicle of the hair is thus continually replaced, cyclically and independently of the adjacent follicles. The anagen phase or growth phase, during which the hair lengthens, lasts several years. The catagen phase, which succeeds the anagen phase, is very short and lasts only a few weeks. During this phase, the hair undergoes an involution, the follicle atrophies and its implantation in the skin appears less and less deep. The telogen phase, which lasts several months, corresponds to a period of rest of the follicle, where the hair finishes by falling out. After this resting phase, a new follicle is regenerated there and a new cycle recommences.

At any moment, not all the hairs are in the same phase at the same time. Thus, out of the approximately 150,000 individual hairs which make up the hair, only approximately 10% of them are at rest and will thus be replaced in a few months according to a biological clock specific to each hair.

In the mouse and other furry mammals, the hair follicles also have a replacement cycle comprising the three anagen, catagen and telogen phases; however, the hair cycles are often "synchronized", that is to say in the same phase of the cycle at the same time in the same region.

The natural loss of the hair can be estimated, on average, at a few hundred hairs per day for a normal physiological state. However, it happens that the hair cycle can go wrong and that hair loss accelerates and results in a temporary or definitive loss of the hair known as alopecia. An alopecia can be caused in different ways.

It may involve a massive loss of or detrimental changes in the hair known as telogen effluvium, after pregnancy, during conditions of undernourishment or dietary imbalances, or also during conditions of asthenia or hormonal dysfunctioning, as may be the case during or after the menopause. It may also involve loss of or detrimental changes in the hair in connection with seasonal phenomena. In certain dermatosis conditions of the scalp with an inflammatory nature, such as, for example, psoriasis or seborrheic dermatitis, hair loss can be greatly increased or can result in highly disrupted cycles of the follicles.

It may also be a matter of alopecia, which is essentially due to a disturbance of hair replacement which results, first, in an acceleration in the frequency of the cycles at the expense of the quality of the hair and then of its amount. The successive growth cycles result in hair which is increasingly fine and increasingly short and which is gradually converted to an unpigmented down. Areas are preferentially affected, in particular the temples or the front of the head, in men, and, in women, a diffuse alopecia of the vertex is observed.

It is a matter more particularly of androgenic alopecia. In a significant number of cases, early hair loss takes place in genetically predisposed subjects; it is then a matter of andro-chronogenetic alopecia. This form of alopecia affects men in particular.

Furthermore, it is known that certain factors, such as hormonal imbalance, physiological stress or malnutrition, can accentuate the phenomenon.

The term alopecia also covers an entire family of conditions of the hair follicle having as a final consequence partial or general definitive hair loss.

For many years, in the cosmetic or pharmacy industry, compositions have been solvent which make it possible to eliminate or reduce alopecia and in particular to induce or stimulate hair growth or to decrease hair loss.

From this viewpoint, a large number of compositions comprising very diverse active principles, are known, such as, for example, 2,4-diamino-6-piperidinopyrimidine 3-oxide or "minoxidil", described in U.S. Pat. Nos. 4,139,619 and 4,596,812, or its numerous derivatives, such as those described, for example, in EP-0353123, EP-0356271, EP-0408442, EP-0522964, EP-0420707, EP-0459890 and EP-0519819.

Clinical studies have demonstrated that $PGF_{2\alpha}$ analogues have the property of bringing about the growth of body hairs and eyelashes in man and animals (Murray A and Johnstone M D, 1997, *Am. J. Opht.*, 124(4), 544-547). In man, tests carried out on the scalp have shown that a prostaglandin $E_2$ analogue (viprostol) has the property of increasing hair density (Roenigk H H., 1988, *Clinic. Dermatol.*, 6(4), 119-121).

WO 98/33497 describes pharmaceutical compositions comprising prostaglandins or prostaglandin derivatives useful to combat hair loss in man. Prostaglandins of the $A_2$, $F_{2\alpha}$ and $E_2$ type are preferred.

Travoprost, alone or in combination, has been provided for stimulating hair growth when applied daily (WO 03/009820, EP-1352629 and EP-1358868).

However, from the above it will be seen that the majority of the products intended to combat hair loss and/or to induce hair regrowth exhibit a demanding dosage for the patient as the administration has to be carried out daily or twice daily. In particular, the dosage recommended for minoxidil, at the dose of 2%, is a twice-daily administration.

Thus, a product with an effectiveness comparable to or greater than that of the products already existing, but which is administered less frequently, i.e., from non-daily to weekly, indeed even twice monthly, will present a major advantage for the patient in terms of comfort and safety of use.

There thus exists a real need to identify and/or develop a product with a less restrictive dosage which would not require daily or twice-daily administration to be as effective, indeed even more effective, than those products identified above.

SUMMARY OF THE INVENTION

It has now transpired that travoprost, administered non-daily, makes it possible to induce a growth of the hair shafts comparable to, and even better than, that obtained with a daily administration. Specifically, in the examples hereinafter presented, it has been demonstrated, surprisingly, that travoprost, administered as a single treatment, induces a growth of human hair follicles in vitro which is comparable to that observed with a repeated treatment with the compound for 7 days (see FIGS. 1 and 3). Furthermore, it has also been demonstrated in vivo, surprisingly, that a single administration of travoprost is more effective with regard to the regrowth of hair shafts than daily administrations (see FIGS. 4 and 5).

The present invention thus features the administration of travoprost or compositions comprised thereof; the travoprost or the composition being useful to stimulate or induce the growth and/or to decrease the loss and/or to increase the density and/or to reduce the heterogeneity in the diameter of the hair shafts in human beings, such compositions being administered according to a time interval from two applications of greater than 24 hours.

More specifically, the present invention features the formulation of travoprost into medicaments for topical application, to stimulate or induce the growth and/or to decrease the loss and/or to increase the density and/or to reduce the heterogeneity in the diameter of the hair shafts in human beings, wherein the regimen for administration of the medicament comprises a time interval from two applications of greater than 24 hours.

In the context of the present invention, the terms dosage (of the application of the composition) and regimen for administration are equivalent.

Application can be carried out non-daily, that is to say, every two, three, four, five, six or seven days. Likewise, the present invention also features weekly, twice weekly, thrice weekly, monthly, twice monthly or thrice monthly application.

The hair shafts are preferably selected from among head hairs, body hairs and eyelashes.

Preferably, the composition is formulated as a medicament.

DETAILED DESCRIPTION OF BEST MODE AND SPECIFIC/PREFERRED EMBODIMENTS OF THE INVENTION

According to a first embodiment of the invention, the composition, more particularly formulated as a medicament, is applied with a time interval from two applications of greater than 24 hours. In this case, topical application is no longer carried out every day (daily or twice daily administrations) but, in contrast, it is carried out every two, three, four, five, six or seven days and should thus be regarded as coming within the field of the present invention.

According to another embodiment, the composition, more particularly formulated as a medicament, is applied in a weekly application.

According to another embodiment of the invention, the composition, more particularly formulated as a medicament, is applied two times (twice weekly) or three times (thrice weekly) per week.

According to another embodiment, the composition, more particularly formulated as a medicament, is applied in one application once per month (monthly).

According to another embodiment, the composition, more particularly formulated as a medicament, is applied once, two times (or twice monthly) or three times per month.

In the context of the present invention, it is possible to envisage administering the composition, more particularly formulated as a medicament, several times according to the time scale defined (weekly or monthly). The practitioner will thus adjust the duration of the treatment according to the result desired, it being possible for the treatment to be thus spread over several months.

Advantageously, the composition, more particularly formulated as a medicament, comprises an amount of travoprost of less than or equal to 0.1% by weight, with respect to the total weight of the composition, more preferably of less than or equal to 0.05%, more preferably of less than or equal to 0.01% to more preferably of from 0.005 and 0.01%.

The present invention thus features the formulation of travoprost into medicaments for topical application.

According to a preferred embodiment, the composition, more particularly formulated as a medicament, comprises approximately 0.01% of travoprost and is intended to be applied in a topical application.

The composition, more particularly formulated as a medicament, is preferably in the form of a lotion, a cream, a salve, a powder or a shampoo or conditioner.

According to one of its embodiments, the compositions are useful to prevent, decrease or slow down hair loss, in particular for the treatment of alopecia, in particular androgenetic alopecia.

This invention also features the cosmetic formulation of travoprost into a cosmetic hair care composition for human beings or into a hair composition for human beings useful to treat androgenic alopecia. Thus, this composition makes it possible to maintain the hair in a good condition and/or to combat natural hair loss in man.

Thus, the present invention features a cosmetic regimen for combating natural hair loss and/or maintaining the hair in a good condition, comprising the topical application of travoprost, the interval from two applications being greater than 24 hours.

The present invention also features a regimen for the treatment of androgenic alopecia, comprising the application of a hair care composition comprising travoprost to an individual requiring such a treatment, the said composition being applied with a time interval from two applications of greater than 24 hours.

In the context of the method for the treatment of androgenic alopecia, the composition is applied every two, three, four, five, six or seven days.

According to an alternative form of the invention, the composition is applied in a weekly, twice weekly, thrice weekly, monthly, twice monthly or thrice monthly application. Preferably, the said composition comprises an amount of travoprost of less than or equal to 0.1%; preferentially, the composition comprises an amount of travoprost of from 0.005 to 0.01%.

The present invention thus features the non-daily application of travoprost, which eliminates a major constraint. The frequency of administration is lower and thus the dosage is different from that which is normally described. Thus, the topical application of the composition according to the invention can be carried out every two, three, four, five, six or seven days. Likewise, the present invention is also targeted at the weekly, twice weekly, thrice weekly, monthly, twice monthly or thrice monthly application.

It is also possible to conduct a sequential treatment in which the frequency will be defined by the treatment sequence. It is possible, in this case, to conduct a first treatment sequence with a particular frequency (for example weekly), followed by a second treatment sequence with a different frequency (for example twice monthly), such as, for example, a treatment defined by a practitioner at the rate of three months with an application once per week and then three months with an application once per month. Different sequences are possible; they will be defined by the practitioner on a case-by-case basis.

Travoprost is a prostaglandin analogue having the following formula:

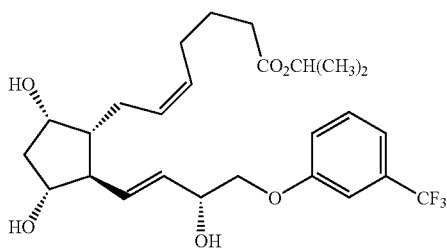

It is fluprostenol isopropyl ester, also known under the chemical name propane-2-yl (Z)-7-[(1R,2R,3R,5S)-3,5-dihydroxy-2-[(1E,3R)-3-hydroxy-4-[3-(trifluoromethyl)phenoxy]but-1-enyl]cyclopentyl]hept-5-enoate, also known under the chemical name isopropyl (Z)-7-[(1R,2R,3R,5S)-3,5-dihydroxy-2-[(1E,3R)-3-hydroxy-4-[(α,α,α-trifluoro-m-tolyl)oxy]-1-butenyl]cyclopentyl]-5-heptenoate. The corresponding acids of travoprost can also be administered according to the invention.

"Heterogeneity in the diameters of the hairs" means a great variation in the diameters of the hairs over the same area of the scalp; some hairs having a physiological diameter from 0.05 to 0.1 mm and others having, in the immediate vicinity of these hairs, a reduced diameter (fine hairs). Thus, "to reduce the heterogeneity in the diameters" means to increase the diameter of the fine hairs.

"To increase the hair density" means to increase the number of hair shafts, hairs or eyelashes per $cm^2$ of skin or scalp.

"Topical application" means application on the superficial body growths, skin, in particular scalp, body hairs and head hairs.

Advantageously, a combination according to the invention will comprise excipients suitable for administration to the cutaneous area or hair shaft targeted, in particular scalp, head hairs, body hairs or eyelashes. The medium in which the travoprost will be formulated according to the invention can be anhydrous or aqueous. The composition comprises, for example, a physiologically acceptable medium which can be composed of water or of at least one solvent selected from hydrophilic organic solvents, lipophilic organic solvents, amphiphilic organic solvents and mixtures thereof, in particular a mixture of water and of at least one of the above-mentioned solvents.

For topical application, the composition according to the invention can be in particular in the form of an aqueous, aqueous/alcoholic or oily solution or of a dispersion of lotion or serum type, of emulsions with a liquid or semi-liquid consistency of the milk type, obtained by dispersion of a fatty phase in an aqueous phase (O/W) or vice-versa (W/O), or multiple emulsions, of a loose or compact powder to be used as is or to be incorporated in a physiologically acceptable medium, or of suspensions or emulsions with a soft consistency of the aqueous or anhydrous gel or cream type, or also of microcapsules or microparticles, or of vesicular dispersions of ionic and/or non-ionic type. It can thus be provided in the form of an ointment, tincture, cream, salve, powder, patch, impregnated pad, solution, emulsion or vesicular dispersion, lotion, gel, spray, suspension, shampoo, aerosol or foam. It can be anhydrous or aqueous. It can also comprise solid preparations constituting cleaning soaps or bars. These compositions are formulated according to the usual methods.

The composition according to the invention can be, in particular, a hair care composition, especially a shampoo or a conditioner, in particular for twice weekly, thrice weekly or weekly application, a hair setting lotion, a treating lotion, a hair care lotion, for example for application every two days or twice weekly, a styling cream or gel, hair restructuring lotions, a mask, and the like.

The cosmetic composition of the invention is preferably a cream, a hair lotion, a shampoo or conditioner, a hair mascara or a mascara for the eyelashes.

For application on the eyelashes or body hairs, the composition according to the invention can be provided in the form of a mascara, which may or may not be pigmented, to be applied with a brush or comb to the eyelashes, eyebrows or hair or also to beard or moustache hairs.

The amounts of the various constituents of the compositions according to the invention are those conventionally used in the fields under consideration.

The aqueous phase comprises water and optionally an ingredient miscible in all proportions with water, such as lower $C_1$ to $C_8$ alcohols, such as ethanol or isopropanol, polyols, such as propylene glycol, glycerol or sorbitol, or also acetone or ether.

When the composition according to the invention is an emulsion, the proportion of the fatty phase can range from 2 to 80% by weight, in particular from 5 to 80% by weight and preferably from 5 to 50% by weight with respect to the total weight of the composition. The oils, waxes, emulsifiers and coemulsifiers included in the composition in the emulsion form are selected from those conventionally employed in the cosmetics field. The emulsifier and the coemulsifier are present in the composition in a proportion ranging from 0.1 to 30% by weight, in particular from 0.3 to 30% by weight, preferably from 0.5 to 20% by weight and better still from 1 to 8% by weight, with respect to the total weight of the composition. The emulsion can additionally comprise lipid vesicles and in particular liposomes.

When the composition according to the invention is an oily solution or gel, the fatty phase can represent more than 90% of the total weight of the composition.

Advantageously, the composition comprises microspheres, nanospheres, liposomes, oleosomes or nanocapsules in which the travoprost is encapsulated. Examples of such formulations are described in particular in EP-375520, EP-447318, EP-557489, WO 97/12602, EP-1151741 or U.S. Pat. No. 5,914,126.

By way of example, the microspheres can be prepared according to the method described in EP-0375520.

The nanospheres can be provided in the form of an aqueous suspension and be prepared according to the methods described in FR-0015686 and FR-0101438.

The oleosomes comprise an oil-in-water emulsion formed by oily globules provided with a lamellar liquid crystal coating dispersed in an aqueous phase (see EP-0641557 and EP-0705593).

The travoprost can also be encapsulated in nanocapsules composed of a lamellar coating obtained from a silicone surfactant as described in EP-0780115; the nanocapsules can also be prepared based on water-dispersible sulfonic polyesters, according to, for example, the technique described in FR-0113337.

Advantageously, for a hair application, the composition is an aqueous, alcoholic or aqueous/alcoholic solution or suspension and better still a water/ethanol solution or suspension. The alcohol fraction can represent from 5 to 99.9% to better still from 8 to 80%.

For a mascara application, the composition is a dispersion of wax-in-water or wax-in-oil, a gelled oil or an aqueous gel, which may or may not be pigmented.

The compositions of the invention can also comprise adjuvants conventional in the cosmetics field, such as hydrophilic or lipophilic gelling or thickening agents, hydrophilic or lipophilic additives, preservatives, antioxidants, solvents, fragrances, fillers, screening agents, odor absorbers, electrolytes, neutralizing agents, UV blocking agents, such as sunscreens, film-forming polymers, cosmetic and pharmaceutical active agents with a beneficial effect on the skin or hair shafts, and coloring materials which are soluble or insoluble in the medium. The amounts of these various adjuvants are those conventionally employed in the cosmetics field and in particular from 0.01 to 50% of the total weight of the composition, for example from 0.01 to 20%, in particular less than or equal to 10% of the total weight of the composition and especially greater than or equal to 0.1%. These adjuvants, depending on their nature, can be introduced into the fatty phase, into the aqueous phase and/or into lipid spherules, vesicles or microspheres, such as liposomes.

The fatty phase can comprise fatty or oily compounds which are liquid at ambient temperature (25° C.) and atmospheric pressure (760 mm of Hg), generally referred to as oils. These oils may or may not be compatible with one another and may form a macroscopically homogeneous liquid fatty phase or a two- or three-phase system.

The fatty phase can, in addition to the oils, comprise waxes, gums, lipophilic polymers, or "pasty" or viscous products comprising solid parts and liquid parts.

Exemplary are, as oils or waxes which can be employed according to the invention, mineral oils (liquid petrolatum, hydrogenated isoparaffin), vegetable oils (liquid fraction of karite butter, sunflower oil, soybean oil, wheat germ oil), animal oils (perhydrosqualene), synthetic oils (purcellin oil, fatty acid esters), silicone oils or waxes (phenyltrimethicone, cyclomethicone, linear or cyclic polydimethylsiloxanes) and fluorinated oils (perfluoropolyethers), beeswax, candelilla wax, carnauba wax or paraffin wax. Free fatty acids (stearic acid, linoleic acid, linolenic acid) and fatty alcohols may be added to these oils and waxes.

Exemplary emulsifiers which can be employed according to the invention are, for example, glycerol stearate or laurate, sorbitol stearates or oleates, alkyl dimethicone copolyols (with alkyl≧8) and mixtures thereof, polyoxyethylenated sorbitol stearate or oleate, for example polysorbate 60 and the PEG-6/PEG-32/Glycol Stearate mixture marketed under the trademark Tefose® 63 by Gattefossè, polyethylene glycol monostearate or monolaurate, dimethicone copolyols and mixtures thereof.

Exemplary solvents which can be employed according to the invention, are lower alcohols, in particular ethanol and isopropanol, or propylene glycol.

Exemplary hydrophilic gelling agents which can be employed according to the invention, are carboxyvinyl polymers (carbomer), acrylic copolymers, such as acrylate/alkylacrylate copolymers, polyacrylamides, polysaccharides, such as hydroxypropylcellulose, natural gums and clays and exemplary are as lipophilic gelling agents, of modified clays, such as Bentones®, metal salts of fatty acids, such as aluminum stearates, hydrophobic silica, ethylcellulose and polyethylene.

In the continuation of the text and unless otherwise indicated, the amounts of the various ingredients of the composition are given as percentage by weight, with respect to the total weight of the composition.

A preferred composition of the invention is a composition to be applied to the scalp.

According to one advantageous embodiment, these compositions additionally comprise at least one agent beneficial for the hair, such as in particular silicones, vegetable, animal, mineral or synthetic oils, waxes, ceramides, pseudoceramides, cationic polymers, sunscreen agents or vitamins.

The silicones which can be employed according to the invention are in particular polyorganosiloxanes which are insoluble in the composition and which can be provided in the form of oils, waxes, resins or gums.

Organopolysiloxanes are defined in more detail in the work by Walter Noll, "Chemistry and Technology of Silicones" (1968), Academic Press. They can be volatile or non-volatile.

Travoprost is preferably the only active principle in promoting hair regrowth and/or limiting hair loss. However, it can also be administered in combination with other compounds active in promoting hair regrowth and/or limiting hair loss.

These compounds can in particular be selected from lipoxygenase inhibitors, such as described in EP 648 488, bradykinin inhibitors, described in particular in EP 845 700, prostaglandins and their derivatives, in particular those described in WO 98/33497, WO 95/11003, JP 97-100091 and JP 96134242, prostaglandin receptor agonists or antagonists, or non-prostanoic prostaglandin analogues, such as described in EP 1 175 891 and EP 1 175 890, WO 01/74307, WO 01/74313, WO 01/74314, WO 01/74315 or WO 01/72268.

Agents which promote hair growth which can be present in the compositions according to the invention include vasodilators, anti-androgens, cyclosporins and their analogues, anti-microbials, anti-fungals, anti-inflammatories, with the exception of selective prostaglandin H synthase-1 or COX-1 inhibitors, or triterpenes, alone or as a mixture.

Vasodilators, such as potassium channel agonists, including minoxidil and its derivatives, aminexil and its derivatives, such as the compounds described in U.S. Pat. Nos. 3,382,247, 5,756,092, 5,772,990, 5,760,043, 5,466,694, 5,438,058, 4,973,474, cromakalim and diazoxide or nicorandil, can thus be included in the compositions.

The anti-androgens which can be used include in particular 5α-reductase inhibitors, such as finasteride and the compounds described in U.S. Pat. No. 5,516,779, cyprosterone acetate, azelaic acid, its salts and its derivatives and the compounds described in U.S. Pat. No. 5,480,913, flutamide and the compounds described in U.S. Pat. Nos. 5,411,981, 5,565, 467 and 4,910,226, RU58841 and Casodex.

The antimicrobial compounds can be selected from among selenium derivatives, ketoconazole, octopirox, triclocarban, triclosan, zinc pyrithione, itraconazole, asiatic acid, hinokitiol, mipirocin, the compounds described in EP-680,745, clinycin hydrochloride, benzoyl peroxide or benzyl peroxide, and minocyclin. The anti-inflammatories can be selected from specific Cox-2 inhibitors, such as, for example, NS-398 and DuP-697 (B. Batistini et al., *DN&P* 1994, 7(8), 501-511) and/or lipoxygenase inhibitors, in particular 5-lipoxygenase inhibitors, such as, for example, zileuton (F. J. Alvarez and R. T. Slade, *Pharmaceutical Res.*, 1992, 9(11), 1465-1473).

Other compounds which are active in promoting hair growth and/or limiting hair loss present in the compositions can also be selected from the group consisting of 6-O-[(9Z, 12Z)-octadeca-9,12-dienoyl]hexapyranose, such as described in FR-027293 and FR-0212828, benzalkonium chloride, benzethonium chloride, phenol, oestradiol, in particular 17α-oestradiol or 17β-oestradiol, chlorpheniramine maleate, chlorophyllin derivatives, cholesterol, cysteine, methionine, benzyl nicotinate, menthol, peppermint oil, calcium pantothenate, panthenol, resorcinol, protein kinase C inhibitors, prostaglandin H synthase-1 or COX-1 activators, such as are described in FR-2732597, glycosidase inhibitors, glycosaminoglycanase inhibitors, pyroglutamic acid esters, hexosaccharidic or acylhexosaccharic acids, aryl-substituted ethylenes, N-acylated amino acids, flavonoids, ascomycin derivatives and analogues, histamine antagonists, triterpenes, such as ursolic acid and the compounds described in U.S. Pat. Nos. 5,529,769, 5,468,888 and 5,631,282, saponins, proteoglycanase inhibitors, oestrogen agonists and antagonists, pseudopterins, cytokines and growth factor promoters, IL-1 or IL-6 inhibitors, IL-10 promoters, TNF inhibitors, vitamins, such as vitamin D, vitamin B12 analogues and pantothenol, hydroxy acids, benzophenones, esterified fatty acids, such as described in FR-027293 and FR-0212828, and hydantoin.

According to one advantageous embodiment of the invention, the travoprost is administered in combination with another compound active in promoting hair growth and/or limiting hair loss, such as a compound selected from prostaglandins, in particular prostaglandin $PGE_1$ and $PGE_2$, their salts, their esters, their analogues and their derivatives, in particular those described in WO 98/33497, WO 95/11003, JP 97-100091 and JP 96134242, especially prostaglandin receptor agonists. It can in particular comprise at least one compound, such as agonists (in the acid form or in the form of a precursor, in particular in the ester form) of the prostaglandin $F_{2\alpha}$ receptor (FP-R), like latanoprost, fluprostenol, cloprostenol, bimatoprost or unoprostone, agonists (and their precursors, in particular esters) of prostaglandin $E_2$ receptors (EP1-R, EP2-R, EP3-R or EP4-R), such as 17-phenyl-$PGE_2$, viprostol, butaprost, misoprostol, sulprostone, 16,16-dimethyl-$PGE_2$, 11-deoxy-$PGE_1$ or 1-deoxy-$PGE_1$, agonists and their precursors, in particular esters, of the prostacyclin (IP) receptor, such as cicaprost, iloprost, isocarbacyclin or beraprost, agonists and their precursors, in particular esters, of the prostaglandin $D_2$ receptor, such as BW245C ((4S)-(3-[(3R,S)-3-cyclohexyl-3-hydroxypropyl]-2,5-dioxo-4-imidazolidineheptanoic acid) or BW246C ((4R)-3-[(3R,S)-3-cyclohexyl-3-hydroxypropyl]-2,5-dioxo-4-imidazolidineheptanoic acid), or agonists and their precursors, in particular esters, of the thromboxane A2 (TP) receptor, such as I-BOP ([1S-[1α,2α(Z),3β(1E,3S),4α]]-7-[3-[3-hydroxy-4-[4-iodophenoxy]-1-butenyl]-7-oxabicyclo [2.2.1]hept-2-yl]-5-heptenoic acid).

According to another embodiment, the composition according to the invention comprises, in addition to the travoprost, advantageously at least one 15-PGDH inhibitor and/or at least one prostaglandin or one prostaglandin derivative, such as, for example, prostaglandins of the 2 series, including in particular $PGF_{2\alpha}$ and $PGE_2$, in the salt form or in the form of precursors, in particular esters (for example, isopropyl esters), their derivatives, such as 16,16-dimethyl-$PGE_2$, 17-phenyl-$PGE_2$, 16,16-dimethyl-$PGF_{2\alpha}$ or 17-phenyl-$PGF_{2\alpha}$, or prostaglandins of the 1 series, such as 11-deoxyprostaglandin $E_1$ or 1-deoxyprostaglandin $E_1$, in a salt or ester form, their analogues, in particular latanoprost, fluprostenol, unoprostone, bimatoprost, cloprostenol, viprostol, butaprost or misoprostol, their salts or their esters.

Preferably, the composition comprises at least one agonist of the FP receptor, such as described, for example, in WO03/009820, or one prostanoic or non-prostanoic agonist of the EP2 and/or EP4 receptors, in particular as described in EP-1175892.

The compositions of the invention can also comprise penetration-accelerating agents. These compounds are known to one skilled in the art and improve the passage of the agents to the site of action; they will be conventionally present in the compositions at concentrations of greater than or equal to 0.01% by weight, in particular from 0.1 to 20% by weight and preferably from 0.1 to 5% by weight, with respect to the total weight of the composition. Compounds of this type which can be used are, for example, urea and the compounds mentioned in WO01/74313.

The statistical analysis is carried out by comparing the effect of travoprost acid at 1 µM in DMSO after a single and repeated treatment, in comparison with the carrier group treated with 0.1% DMSO.

$p>0.05$=NS; $0.01<p<0.05$=*; $0.001<p<0.01$=; $p<0.001$=*

Figure 4:
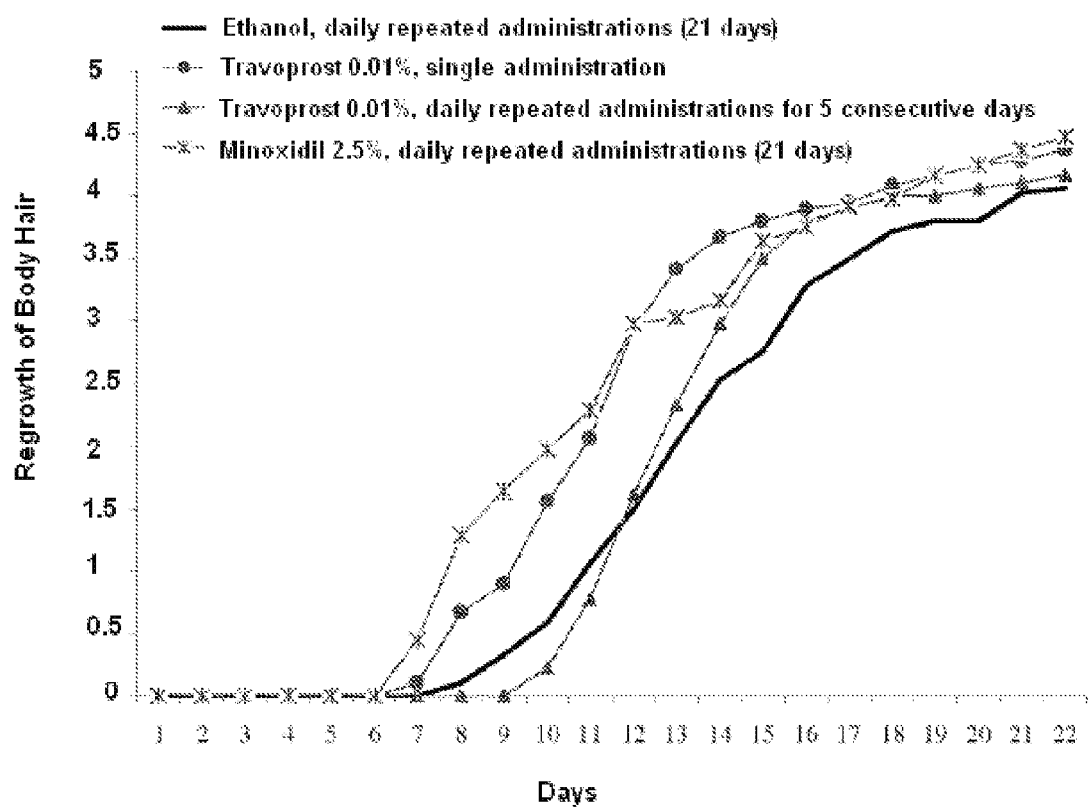

FIG. 4 is a graph comparing the effect on the change in the regrowth of the body hair in the C57BL/6 mouse of the ethanol carrier in repeated daily administration for 21 days, of 2.5% minoxidil in repeated daily administration for 21 days, of 0.01% travoprost in repeated daily administration for 5 consecutive days and of 0.01% travoprost in a single administration.

Figure 5:
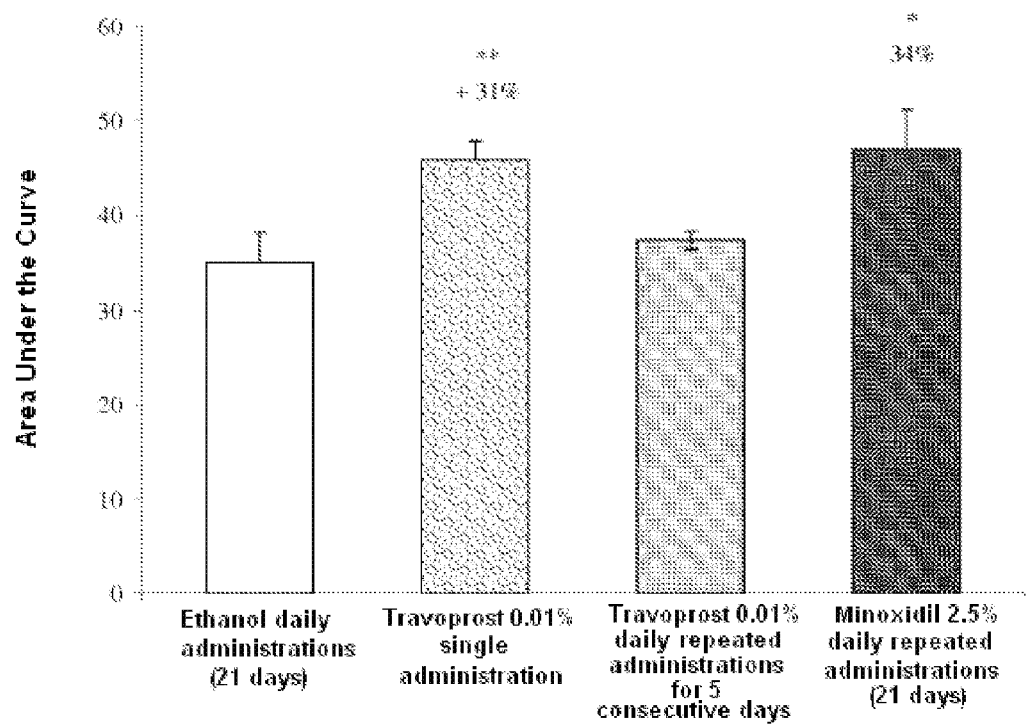

FIG. 5 is a graph comparing the effect on the change in the regrowth of the body hair in the C57BL/6 mouse, expressed by the area under the curve, of the ethanol carrier in repeated daily administration for 21 days, of 2.5% minoxidil in repeated daily administration for 21 days, of 0.01% travoprost in repeated daily administration for 5 consecutive days and of 0.01% travoprost in a single administration $p>0.05$=NS; $0.01<p<0.05$=*; $0.001<p<0.01$=; $p<0.001$=*

To further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Human Hair Follicles Kept Alive

1: Methods

Human hair follicles are dissected while keeping the bulb and the connective and epithelial sheaths intact to be cultured in an appropriate medium which makes it possible to provide for the growth of the follicle ex vivo while keeping its structure intact in the growth or anagen phase (Stenn, Ann. N.Y. Acad. Sci., 1991, Dec. 26, 642, xi-xiii). The growth of the hair follicles in vitro is then evaluated using the measurement of elongation of the internal sheath.

A°/Organ Culture:

Human hair follicles of "terminal" type are isolated from a skin sample resulting from facial surgery (lifting). For this, the skin is cut into pieces of approximately 5×5 mm. The hypodermis is separated from the dermis using a scalpel blade. The hair follicles are isolated from the hypodermal part under a binocular magnifier using fine forceps. Only the hair follicles in the growth phase with a bulb and intact connective and epithelial sheaths are retained for study.

The hair follicles thus isolated are incubated at 37° C. in a humid atmosphere (5% $CO_2$ and 95% air) and are cultured individually in suspension for 7 days in William's E medium supplemented with 2 mM of L-glutamine, 10 µg/ml of insulin, 10 ng/ml of hydrocortisone and 1% of antibiotics/antimitotics. The culture medium is replaced every 2 or 3 days.

B°/Treatment:

The travoprost in its acid form is taken up in DMSO at a concentration of $10^{-2}$M and stored at $-20°$ C. until used.

The surviving hair follicles are treated with the DMSO carrier at a final concentration of 0.1% or with the travoprost acid at a concentration of 1 µM in DMSO (final DMSO concentration also at 0.1%). For each condition, 22 hair follicles are treated individually subsequent to culturing at D0. In the case of a repeated treatment, the travoprost acid at 1 µM in DMSO is replaced at the time of the change in medium, this being done for 7 days. In the case of a single treatment, the travoprost acid at 1 µM DMSO is added to the culture medium just once in the culturing.

C°/Measurement of the Growth of the Hair Follicles In Vitro:

The growth of the hair follicles is determined by the measurement of the elongation of the hair shaft from day D0 to day D7. The elongation of the hair shaft is analyzed using Tina image analysis software. The measurements are carried out on hair follicles isolated at days D0, D3, D5 and D7.

D°/Statistical Analysis:

For a Hair Follicle:

The mean post-D0 length (by definition: the mean of the lengths measured on the days following D0) is considered:

The mean post-D0 length is a function:
 of the initial length at D0
 of the treatment group
 of other factors related to technological or biological variability.

The effect of the treatment can be estimated and can be combined with a significance-probability that the estimated level of the effect can be the result of chance, that is to say, under the hypothesis (referred to as "null" hypothesis) where there is no real effect.

A. Preliminary Screening:

The hair follicles exhibiting a "suspect" morphology at the end of the study are excluded from the analysis. In this study example, 15 hair follicles (all groups mixed up) out of 66 cultured were discarded.

B. Statistical Model:

It is assumed that the mean post-D0 length is the sum of four components:

The "natural" effect of time on the elongation of the hair shaft in the presence of DMSO.

The additional effect in the presence of the product (which may be positive or negative).

An effect proportional to the initial length (length at D0). The coefficient of proportionality may be dependent on the group.

A random effect related to technological or biological variability.

C. Robust ANOVA Test:

Some measurements, referred to as "aberrant" measurements, can have a highly disruptive effect on the estimation of the effects of the model. A robust ANOVA method is applied with regard to these measurements: "LTS" (Least Trimmed Squares). The principle of the LTS method is as follows:

1. A definition is made at the start of a fixed proportion p0 of observations which it is desired to ignore in the estimation of the effects (p0=10%) among all the observations present independently of the treatment (observations of the entire study). The corresponding number of observations is denoted n0.

2. n0 points are selected at random and excluded from the estimation process.

3. The parameters (effects) of the model are estimated.

4. Among the observations, excluded and non-excluded, the n0 observations which are the least well predicted by the model are identified.

5. The n0 least well predicted observations found in stage 4, are, in their turn, excluded from the estimation process.

6. Stage 3 (estimation) is reverted to until the observations excluded in stage 5 remain unchanged ("convergence").

It should be noted that the exclusion method is completely independent of the question posed (significant effect of the treatment).

In view of the random selection carried out in stage 2 of the LTS process, the solution (in terms of points excluded after convergence) is generally not unique. Consequently, the estimation of the effects of the model depends on the initial random selection.

The LTS process is repeated a large number of times (200) starting from different random selections. Among the 200 models found, the choice is made of that which minimizes the difference from the coefficients of proportionality associated with each of the groups which connect the initial length with the mean post-D0 length (optimization of the parallelism). This process of optimization of the parallelism guarantees that the additive effect of the treatment is identical, whatever the initial length of the follicle (no significant interaction from treatment and slope of the straight line).

This process made possible the exclusion of 6 follicles out of a total of 51 follicles used in the statistical analysis.

D. Interference Tests:

For each of the groups treated, a test is carried out on the significance of the additional effect of the product in comparison with the control group (construction of the contrasts: Effect(Treated i)−Effect(Control) for each treated group i).

The significance is adjusted by the number of tests carried out (=number of groups treated).

2. Results

For each treatment, the elongation is expressed in cumulative mm from day D0 [mean±SEM (n=22 at D0)]. The area under the curve (the sum of the total lengths of each hair follicle) is also calculated from day D0 to D7 for each condition [mean±SEM (n=22 at D0)].

Figure 1:
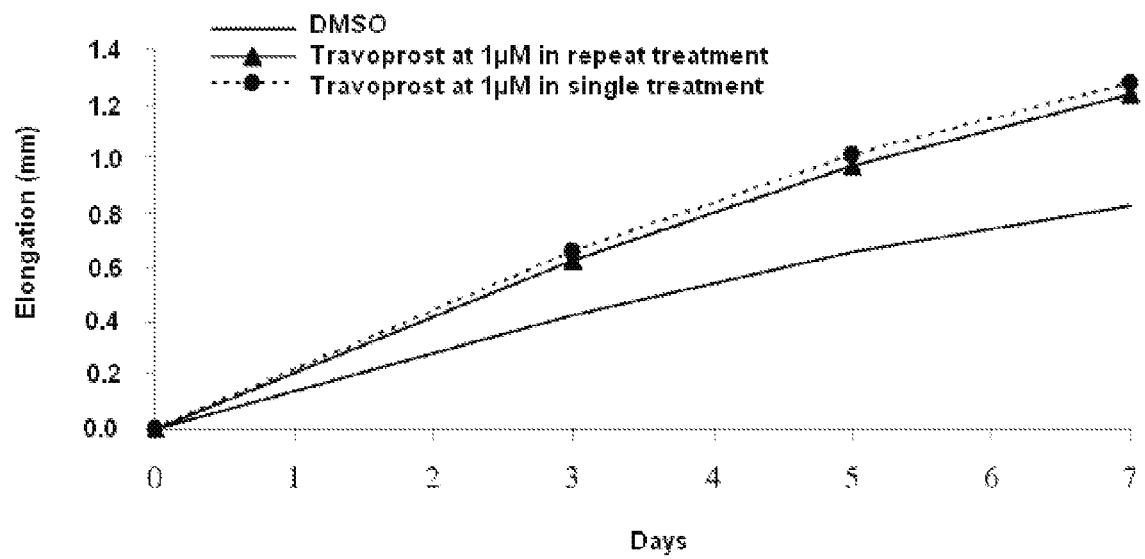
FIG. 1 is a graph comparing the effect of travoprost acid 1 µM, after a single treatment at the time of culturing and after repeated treatment lasting 7 days, on the elongation of the hair shaft of human hair follicles kept alive (expressed in mm) as a function of the time.
Figure 2:
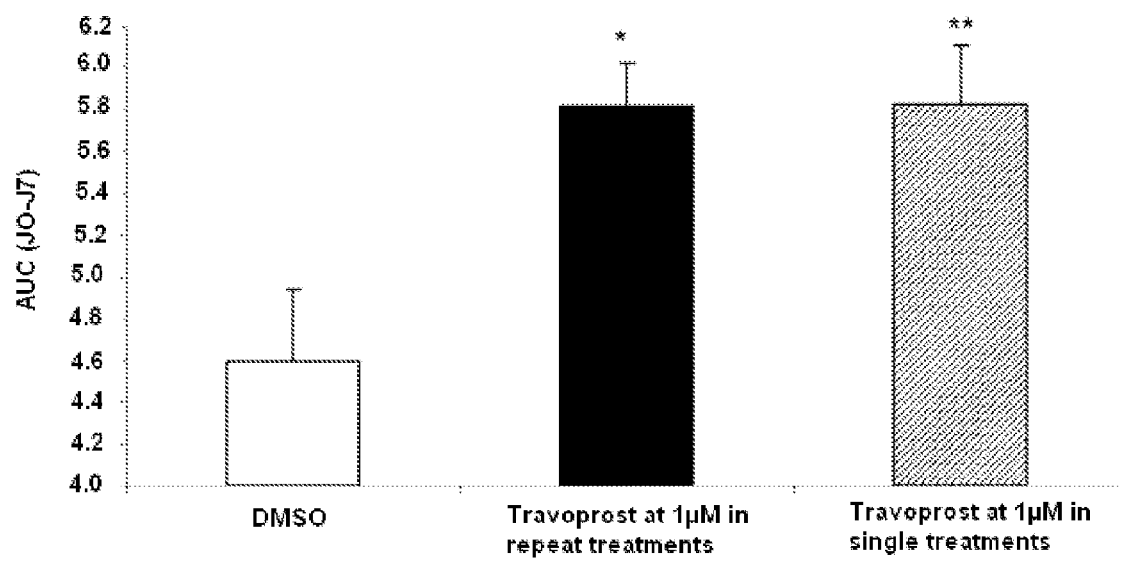
FIG. 2 is a graph comparing the effect of travoprost acid 1 µM, after a single treatment at the time of culturing and after treatment during 7 days, on the elongation of the hair shaft of human hair follicles kept alive represented by the area under the curve from D0 to D7.

The results presented in FIGS. 1 and 2 and summarized in the table below show that, as described in the literature, the elongation of the hair follicles after treatment with the carrier DMSO is approximately 0.15 mm per day. A single treatment with travoprost acid at a concentration of 1 µM in DMSO induces an elongation in the hair shaft of the human hair follicles kept alive which is greater than that obtained with the carrier DMSO. This effect appears from the third day of treatment. The kinetics and the amplitude of response observed after a single treatment at the time of culturing with travoprost acid at 1 µM in DMSO is comparable with that obtained after a repeated treatment during the 7 days of culturing.

Figure 3:
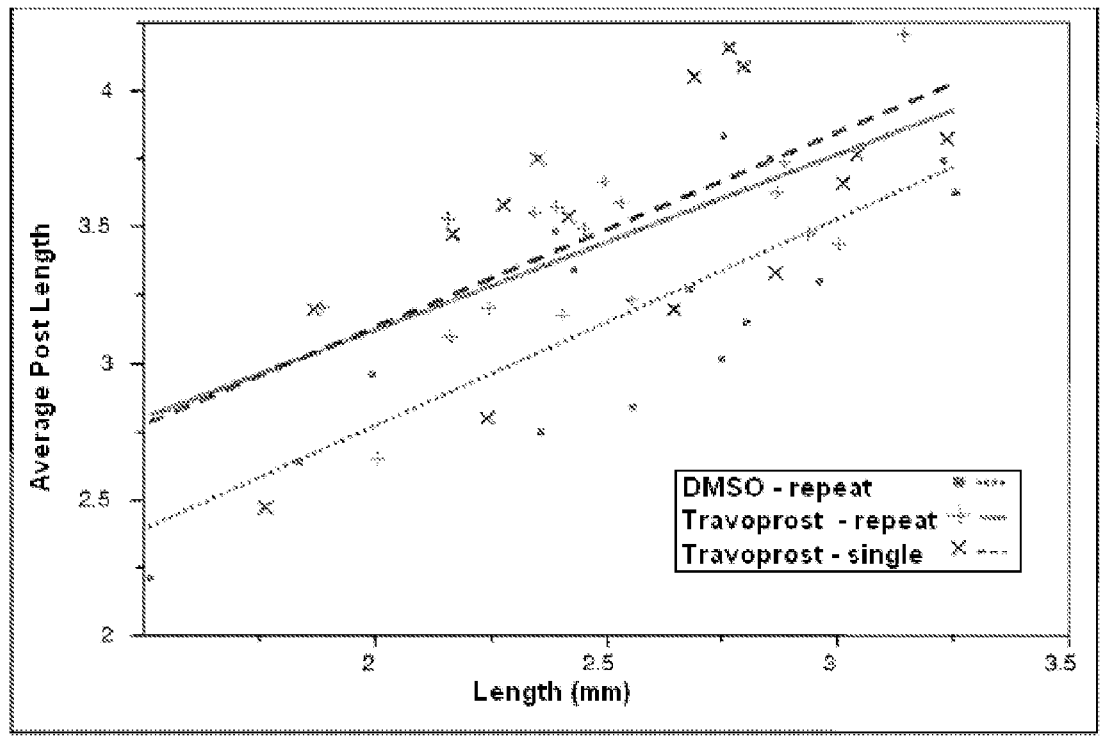
FIG. 3 is a graph showing the statistical analysis of the experiment described in FIG. 1.

The results of the statistical analysis presented in FIG. 3 show that the inductive effect of travoprost after a single or repeated treatment is significantly different from that observed with the carrier DMSO.

| Treatment | Elongation at D 7 (mm) | AUC (D 0-D 7) | Significance |
|---|---|---|---|
| DMSO | 0.82 | 4.60 | |
| Travoprost at 1 µM in repeated treatment | 1.23 | 5.82 | * |
| Travoprost at 1 µM in a single treatment | 1.27 | 5.83 | ** |

3. Conclusions

This example demonstrates that travoprost in repeated treatment significantly induces the growth of human hair follicles in vitro. Surprisingly, this example also shows that travoprost in a single treatment induces the growth of the hair follicles in a similar way, in terms of kinetics and of amplitude of response, as travoprost in repeated treatment.

This result indicates that a repeated treatment in man, that is to say a daily treatment, will not be essential in stimulating or inducing the growth of the hair follicles.

The effect of travoprost was thus evaluated in the model of regrowth of the body hair in the C57BL/6 mouse to validate these results in vivo.

Example 2

Model of Regrowth of the Body Hair in the C57BL/6 Mouse

1. Methods

The C57BL/6 mice are each a particularly useful model for the study of hair growth:

In C57BL/6 mice, the fur is black. In the trunk of the animals, the melanocytes are present solely in the hair follicles and the production of pigment is strictly correlated with the anagen phase of the hair cycle (Slominski A. and Paus R., J. Invest. Dermatol., 10, 90S-97S, 1993).

In young mice, the hair cycles are not in phase throughout the body but are synchronized in a region according to a rostro-caudal wave (Hale P. A. and Ebling F. J., *J. EXP. Zool.*, 191, 49-62). At 42 days, the hair follicles of the dorsal region enter the telogen phase (Chase H. B. *Physiol. Rev.*, 34, 113-126, 195).

Thus, after clipping and shaving the backs of C57BL/6 mice aged 42 days, the regrowth can be easily visualized before the hair shafts appear at the surface by the grey appearance which the skin assumes. The delay in appearance of the grey color of the skin and the delay in appearance of the hair shafts after clipping and shaving represent criteria which give an account of the rate of entry of the hair follicle into the anagen phase and the rate of growth of the hair shaft. These two criteria will thus be used to evaluate the activity on the hair growth of the compounds tested.

A°/Model:

The male C57BL/6 mice are aged 42 days at the beginning of the study. The groups are formed of 10 animals.

On day D0, the backs of the animals are clipped with Minicut clippers equipped with a shoe (retention of 4 mm of hair shaft) and shaved with a Braun razor. Twenty-four hours after clipping and shaving, on day D1 of the study, a clinical observation is carried out and only the mice exhibiting a uniformly pink skin and unharmed by skin injuries are selected for introduction into the study.

The study is carried out over 21 days.

| Day of the study | Actions |
|---|---|
| D-5 | Reception of the animals and acclimatization |
| D 0 | Anaesthesia, clipping and shaving of the animals |
| D 1 | Selection, randomization and introduction into the study of the animals |
| D 1 to D 21 | Treatment at the clipped and shaved area |
| D 1 to D 22 | Clinical observations |
| D 1 to D 21 | Evaluation of the hair growth |
| D 22 | Euthanasia of the animals |

The hair growth is evaluated according to the criteria defined in:

| Scores | Clinical appearance |
|---|---|
| 0 | Uniformly pink skin |
| 1 | Appearance of grey-colored marks on the clipped and shaven surface |
| 2 | Appearance of the first hair shafts on the clipped and depilated surface |
| 3 | Grey color over the whole of the clipped and depilated surface |
| 4 | Presence of hair shafts over the whole of the clipped and depilated surface |
| 5 | Uniform regrowth of body hairs from the clipped/depilated surface and the non-depilated surface |

B°/Treatment:

Minoxidil in solution in ethanol at 2.5% is used as positive control of the regrowth of the body hair.

Travoprost in its isopropyl ester form is used in solution in ethanol at 0.01%.

The travoprost, the minoxidil and the carrier are administered by the topical route using a pipette at the rate of 50 µl per application.

The minoxidil and the carrier are administered in repeated daily fashion from day 1 to day 21 of the study. Two different treatments are carried out with the travoprost: a first group receiving a single administration on day 1 of the study and a second group receiving five repeated daily and consecutive administrations from day 1 to day 5 of the study.

C°/Evaluation of the Regrowth and Statistical Analysis:

The following calculations are carried out:

Mean±SEM of the scores per day for each group treated.

Areas under the curve (AUC) of the regrowth scores per animal from D1 to D22.

Mean±SEM of the AUC values per treatment group.

Percentage of increase in the AUC values for each treated group versus the carrier group.

The AUC is obtained by summing the areas of the rectangles from the first and the final day of the study. The different treatment groups are compared with the carrier group with regard to this parameter by means of a Student's t-test.

2. Results

The results presented in FIGS. 4 and 5 and in the table of results below show that the minoxidil, in repeated daily administration for 21 days at the dose of 2.5%, accelerates the regrowth of the body hair in comparison with the ethanol carrier. Surprisingly, a single administration of travoprost at 0.01% significantly accelerates the regrowth of the body hair in comparison with the carrier with an amplitude of response (31%) identical to that obtained after repeated daily treatment of minoxidil at 2.5% (30%).

Contrary to all expectations, repeated daily and consecutive administrations for 5 days of travoprost at 0.01% do not accelerate the regrowth of the body hairs.

| Treatment | Regrowth of the body hair versus ethanol ΔAUC (D 1-D 22) | p value (Student's t-test) | Significance |
|---|---|---|---|
| Minoxidil at 2.5% repeated daily administrations (21 days) | +34% | 0.035 | * |
| Travoprost at 0.01% repeated daily administrations (5 days) | +7% | 0.506 | NS |
| Travoprost at 0.01% single administration | +31% | 0.011 | ** |

3. Conclusions

This second example demonstrates, surprisingly, that travoprost, after a single administration, significantly accelerates the in vivo regrowth of the body hair in the mouse. This effect is comparable to that observed with the reference compound minoxidil used in repeated daily administration. However, contrary to all expectations, travoprost used in repeated consecutive daily administrations for 5 days is less effective with regard to the in vivo regrowth of the body hair. A single in vivo administration of travoprost is thus more effective with regard to the induction of the growth of the hair follicles than a repeated daily administration.

Examples 1 and 2 thus show that travoprost induces the growth of the hair follicle in vitro and in vivo in a comparable way, indeed even a more effective way, after single administration than after repeated daily administration.

These combined studies support administration of travoprost in man according to a suitable dosage, namely, a non-daily application according to the present invention, which makes possible maximum effectiveness of the compound to obtain a stimulation or induction of the growth of the hair follicles.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A non-daily method for stimulating or inducing the growth and/or decreasing the loss and/or increasing the density and/or reducing the heterogeneity in the diameter of hair follicles in a human subject, comprising topically applying a thus effective amount of a medicament composition which comprises from 0.005 to 0.01% travoprost onto such hair follicles, for such non-daily period of time as required to elicit the desired effect, wherein at least two non-daily topical applications are carried out at a time interval between them of every two, three, four, five or six days, or weekly, or once, twice or three times monthly wherein the travoprost is the only prostaglandin hair growth active agent in the medicament composition.

2. The non-daily method as defined by claim 1, comprising such topical application every four, five or six days.

3. The non-daily method as defined by claim 1, comprising a weekly topical application.

4. The non-daily method as defined by claim 1, comprising a monthly topical application.

5. The non-daily method as defined by claim 1, comprising a twice or thrice monthly topical application.

6. The non-daily method as defined by claim 1, in which said medicament comprises a lotion, a cream, an emulsion, a salve, a mascara, a powder, a shampoo or a conditioner.

7. The non-daily method as defined by claim 1, said hair follicles comprising head hairs, body hairs and/or eyelashes.

8. The non-daily method as defined by claim 1, wherein said subject is in need of treatment of androgenic alopecia.

9. The non-daily method as defined by claim 8, in which said medicament composition is topically applied every four, five or six days, or weekly, or once, twice or three times monthly.

10. A non-daily method for the treatment of androgenic alopecia, comprising topically applying a thus effective amount of a medicament composition which comprises from 0.005 to 0.01% travoprost onto the scalp of an individual in need of such treatment, for such non-daily period of time as required to elicit the desired effect, wherein at least two non-daily topical applications are carried out at a time interval between them of every two, three, four, five or six days, or weekly, or once, twice or three times monthly wherein the travoprost is the only prostaglandin hair growth active agent in the medicament composition.

* * * * *